United States Patent [19]

Scartazzini

[11] 4,301,279
[45] Nov. 17, 1981

[54] PROCESS FOR THE PRODUCTION OF 3-HYDROXY COMPOUNDS

[75] Inventor: Riccardo Scartazzini, Basel, Switzerland

[73] Assignee: Ciba-Geigy Corporation, Ardsley, N.Y.

[21] Appl. No.: 121,085

[22] Filed: Feb. 13, 1980

[30] Foreign Application Priority Data

Feb. 23, 1979 [CH] Switzerland .................. 1844/79

[51] Int. Cl.³ .......................................... C07D 501/20
[52] U.S. Cl. .................................... 544/016; 544/22; 424/246
[58] Field of Search ........................... 544/16, 30, 22; 424/246

[56] References Cited

U.S. PATENT DOCUMENTS 3,193,550 7/1965 Harris ................................. 544/30
3,989,695 11/1976 Scartazzini ..................... 260/243 C

FOREIGN PATENT DOCUMENTS 327381 1/1976 Austria.
2331078 1/1974 Fed. Rep. of Germany.
2331148 1/1974 Fed. Rep. of Germany.
2506330 9/1975 Fed. Rep. of Germany.
2606196 9/1976 Fed. Rep. of Germany.

Primary Examiner—Nicholas S. Rizzo
Attorney, Agent, or Firm—Prabodh I. Almaula

[57] ABSTRACT

Process for the production of 7β-substituted 3-hydroxycepham-4-carboxylic acid compounds of the formula

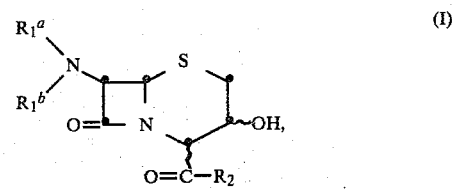

in which
$R_1^a$ represents hydrogen or an amino-protecting group $R_1^A$, and
$R_1^b$ represents hydrogen or an acyl radical Ac,
or in which
$R_1^a$ and $R_1^b$ together form a bivalent amino-protecting group, and
$R_2$ represents a radical that, together with the carbonyl grouping —C(=O)—, forms a protected carboxyl group,
and 1-oxides thereof as well as salts of such compounds with salt-forming groups, from a 7β-substituted 3-hydroxy-3-cephem-4-carboxylic acid compound of the formula

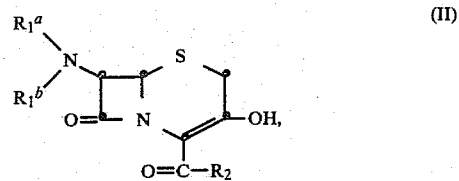

from a 1-oxide or a salt thereof, and a complex borohydride, characterized in that the reduction is carried out in the presence of an organic acid.

The reduction in the presence of an organic acid produces higher yields.

13 Claims, No Drawings

PROCESS FOR THE PRODUCTION OF 3-HYDROXY COMPOUNDS

The invention relates to a new process for the production of cepham compounds, especially 7β-substituted 3-hydroxycepham-4-carboxylic acid compounds which are valuable intermediates for the production of antibiotically active 7β-substituted 3-cephem-4-carboxylic acid compounds. The invention relates especially to a process for the production of 7β-substituted 3-hydroxycepham-4-carboxylic acid compounds from 7β-substituted 3-hydroxycepham-4-carboxylic acid compounds by reduction by means of complex borohydrides in the presence of organic acids.

The production of 7β-substituted 3-hydroxycepham-4-carboxylic acid compounds from 7β-substituted 3-hydroxy-3-cephem-4-carboxylic acid compounds and from the tautomeric form thereof, 7β-substituted 3-oxocepham-4-carboxylic acid compounds, by reduction by means of catalytically activated hydrogen, metallic reducing agents (nascent hydrogen) and with hydride reducing agents has already been described in German Offenlegungsschrift No. 2,331,078. The use of an aqueous solution of sodium borohydride in methanol was specifically described.

The results obtained with the reducing agents described proved to be unsatisfactory, especially with regard to the yields. There was therefore a need for an economically more favourable process.

It has been found, surprisingly, that in the reduction of the mentioned 3-hydroxy-3-cephem-4-carboxylic acid compounds with a complex borohydride substantially higher yields of the corresponding 3-hydroxycepham compounds and also purer products are obtained if the reaction is carried out in the presence of an organic acid.

The subject of the present invention is a process for the production of 7β-substituted 3-hydroxycepham-4-carboxylic acid compounds of the formula

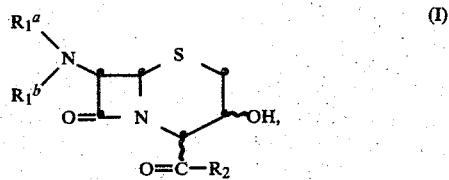

in which
R₁ᵃ represents hydrogen or an amino-protecting group $R_1^A$, and
R₁ᵇ represents hydrogen or an acyl radical Ac,
or in which
R₁ᵃ and R₁ᵇ together form a bivalent amino-protecting group, and
R₂ represents a radical that, together with the carbonyl grouping —C(=O)—, forms a protected carboxyl group,
and 1-oxides thereof as well as salts of such compounds with salt-forming groups, from a 7β-substituted 3-hydroxy-3-cephem-4-carboxylic acid compound of the formula

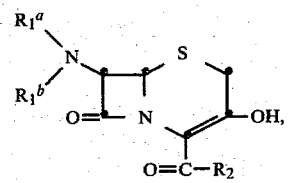

from a 1-oxide or a salt thereof, and a complex borohydride, characterised in that the reduction is carried out in the presence of an organic acid.

In the compounds of the formula I, the 3-hydroxy group and the protected 4-carboxy group are in the α- or β-configuration, the α-configurations being preferred for both groups since, during the reduction, they are steered preferably into these configurations.

The starting compounds of the formula II may also be in the tautomeric 3-oxocepham form.

In the following description of the invention, the term "lower" in groups such as lower alkyl, lower alkylene, lower alkoxy, lower alkanoyl and the like means that the corresponding groups, unless expressly defined otherwise, contain up to 7, preferably up to 4, carbon atoms.

The functional groups present in compounds of the formula I or II, especially carboxyl, amino, hydroxy, hydroxyimino and sulpho groups, are optionally protected by protecting groups that are used in penicillin, cephalosporin and peptide chemistry.

Such protecting groups can readily be split off, that is to say without undesired side-reactions occurring, for example by solvolysis, reduction, photolysis or also under physiological conditions.

Protecting groups of this kind and the methods by which they are split off are described, for example, in "Protective Groups in Organic Chemistry", Plenum Press, London, New York, 1973, also in "The Peptides", Vol. I, Schröder and Lübke, Academic Press, London, New York, 1965 and also in Houben-Weyl, "Methoden der organischen Chemie", 4th edition, Vol. 15/1, Georg Thieme Verlag, Stuttgart, 1974.

In the starting products of the formula II and in the end product of the formula I, the symbols $R_1^A$, $R_1^b$, Ac and $R_2$ have, for example, the following meanings:

An amino-protecting group $R_1^A$ is a group that can be replaced by hydrogen, especially an acyl group Ac, also a triarylmethyl group as well as an organic silyl or stannyl group.

An acyl group Ac, which may also represent the radical $R_1^b$, is especially the acyl radical of an organic carboxylic acid, preferably having up to 18, and especially up to 10, carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid and represents especially an acyl radical of an organic carboxylic acid present in a naturally occurring or in a bio-synthetically, semi-synthetically or entirely synthetically producible, preferably pharmacologically active, N-acyl derivative of a 6-amino-penam-3-carboxylic acid compound or a 7-amino-3-cephem-4-carboxylic acid compound, preferably having up to 18, especially up to 10, carbon atoms.

Such an acyl radical Ac is especially a group of the formula

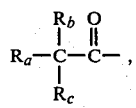 (IA)

in which (1)
$R_a$ represents an optionally substituted carbocyclic aryl radical, for example a corresponding phenyl radical, an optionally substituted, preferably unsaturated, cycloaliphatic hydrocarbon radical, for example corresponding cyclohexadienyl or cyclohexenyl, or an optionally substituted heterocyclic aryl radical, for example corresponding thienyl, furyl or thiazolyl,
$R_b$ represents hydrogen, and
$R_c$ represents hydrogen or optionally substituted, especially protected, hydroxy, amino, carboxyl or sulpho,
or in which (2)
$R_a$ represents optionally protected ω-amino-ω-carboxy-lower alkyl, for example ω-amino-ω-carboxypropyl, cyano etherified hydroxy or mercapto, such as optionally substituted phenoxy, phenylthio, or pyridylthio, or an optionally substituted, unsaturated heterocyclic radical linked by a ring nitrogen atom, for example the corresponding tetrazolyl radical, and
$R_b$ and $R_c$ represent hydrogen,
or in which (3)
$R_a$ represents an optionally substituted carbocyclic aryl radical, for example a corresponding phenyl radical, or an optionally substituted heterocyclic aryl radical, for example a corresponding thienyl, furyl or thiazolyl radical, and
$R_b$ and $R_c$ together represent preferably O-substituted hydroxyimino in the syn configuration.

Cyclohexadienyl is especially 1,4-cyclohexadienyl, whilst cyclohexenyl is especially 1-cyclohexenyl.

Thienyl is preferably 2-thienyl and also 3-thienyl, furyl denotes especially 2-furyl, thiazolyl is especially 4-thiazolyl, whilst pyridylthio represents, for example, 4-pyridylthio, and tetrazolyl represents, for example, 1-tetrazolyl.

Substituents of a phenyl or phenoxy group $R_a$ may be present in any position and are, inter alia, aliphatic hydrocarbon radicals, such as optionally substituted lower alkyl, for example protected aminomethyl, optionally functionally modified, such as etherified or esterified, hydroxy, or optionally substituted, especially protected, amino, such as acylamino, or nitro which, for example, in the phenoxy group, may be in the 2-position.

Substituents of a cyclohexadienyl or cyclohexenyl group as well as of a thienyl or furyl group $R_a$ are, for example, optionally substituted lower alkyl, such as optionally substituted, for example protected, aminomethyl, a substituent of this type, especially optionally protected aminomethyl, being especially in the 2-position of a 1,4-cyclohexadienyl or 1-cyclohexenyl radical or in the 5-position of a 2-thienyl or 2-furyl radical. Substituted thiazolyl is especially 2-amino-4-thiazolyl, the amino group being optionally protected or substituted by lower alkyl, especially $C_1$–$C_4$-lower alkyl, for example methyl, ethyl, propyl, isopropyl, butyl or tert.-butyl.

Optionally protected aminomethyl is especially aminomethyl optionally substituted by lower alkyl, for example methylaminomethyl, amino being optionally protected, whilst etherified hydroxy may be, for example lower alkoxy, such as methoxy, and esterified hydroxy may be, for example, lower alkanoyloxy, such as acetoxy, aroyloxy, for example benzoyloxy, carbamoyloxy or halogen, for example chlorine, and optionally substituted amino may be, for example, amino substituted by lower alkyl, for example methylamino, or lower alkylsulphonylamino, for example methylsulphonylamino.

Protected hydroxy, amino, carboxyl or sulpho groups in acyl radicals of the formula IA are those which are customary in penicillin and cephalosporin chemistry and can readily be converted into free hydroxy, amino, carboxyl or sulpho groups without the cephem structure being destroyed or other undesired side reactions occurring.

Amino groups can be protected, for example, by acyl radicals, an acyl radical being especially an acyl radical of a semi-ester of carbonic acid which can be split off by reduction, for example by treating with a chemical reducing agent or with catalytically activated hydrogen, or by solvolysis, for example treating with a suitable acid, and also by means of radiation, such as a lower alkoxycarbonyl radical which is preferably polybranched at the first carbon atom of the esterifying group and/or substituted by aryl, for example phenyl or biphenylyl optionally substituted such as by lower alkoxy, for example methoxy and/or by nitro, or by arylcarbonyl, especially benzoyl, for example, tert.-butoxycarbonyl, tert.-pentyloxycarbonyl, diphenylmethoxycarbonyl, 1-(4-biphenylyl)-1-methylethoxycarbonyl, benzyloxycarbonyl, 4-nitrobenzyloxycarbonyl, 2-nitro-4,5-dimethoxybenzyloxycarbonyl or phenacyloxycarbonyl, or a lower alkoxycarbonyl radical substituted at the second carbon atom of the esterifying group by halogen, for example 2,2,2-trichloroethoxycarbonyl or 2-iodoethoxycarbonyl (or a radical that can be converted into the latter, such as 2-chloroethoxycarbonyl or 2-bromomethoxycarbonyl), or alternatively polycyclic cycloalkoxycarbonyl, for example adamantyloxycarbonyl.

An amino group can also be protected by an arylmethyl radical, such as a polyarylmethyl radical, for example by trityl; a 2-carbonylvinyl grouping, such as a 1-lower alkoxycarbonyl-1-propen-2-yl group, for example 1-methoxycarbonyl-1-propen-2-yl; an arylthio or aryl-lower alkylthio group, for example 2-nitrophenylthio or pentachlorophenylthio, also tritylthio, or an arylsulphonyl group; also by an organic silyl or stannyl group, such as a silyl or stannyl group substituted by lower alkyl, halo-lower alkyl, cycloalkyl, phenyl or phenyl-lower alkyl, or by optionally functionally modified groups, such as lower alkoxy, for example methoxy, or by halogen, for example chlorine, especially tri-lower alkylsilyl, for example trimethylsilyl, halolower alkoxy-lower alkylsilyl, for example chloromethoxymethylsilyl, or also tri-lower alkylstannyl, for example tri-n-butylstannyl.

Hydroxy-protecting groups are, for example, acyl radicals, especially one of the acyl radicals of carbonic acid semi-esters mentioned in connection with a protected amino group, or organic silyl or stannyl radicals, also 2-oxa- or 2-thia-aliphatic or 2-oxa- or 2-thia-cycloaliphatic hydrocarbon radicals that can readily be split off, especially 1-lower alkoxy-lower alkyl or 1-lower alkylthio-lower alkyl, for example 1-methoxyethyl, 1-ethoxyethyl, 1-methylthioethyl or 1-ethylthioethyl, or 2-oxa- or 2-thia-cyclolower alkyl having from 5 to 7 ring atoms, for example 2-tetrahydrofuryl or 2-tetrahydropyranyl or corresponding thia analogues, as well as optionally substituted α-phenyl-lower alkyl radicals that can readily be split off, such as optionally substituted benzyl or diphenylmethyl, the substituents of the phenyl radicals being, for example, halogen, such as chlorine, lower alkoxy, such as methoxy, and/or nitro.

A protected carboxyl or sulpho group is especially a carboxyl or sulpho group esterified with an aliphatic, cycloaliphatic, cycloaliphatic-aliphatic, aromatic or araliphatic alcohol, such as a lower alkanol, or with a silyl or stannyl radical, such as tri-lower alkylsilyl. In a carboxyl or sulpho group, the hydroxy group can be etherified, for example, in the same manner as the hydroxy group in an esterified carboxy group of the formula —C(=O)—$R_2$.

O-substituted hydroxyimino is especially lower alkoxyimino, for example methoxyimino or ethoxyimino, also phenoxyimino or phenyl-lower alkoxyimino, for example benzyloxyimino, such groups being preferably in the syn form.

An amino group protected by an amino-protecting group $R_1^A$ may also be, for example, an amino group protected by the acyl radical of a carbonic acid semiester, a 2-carbonylvinyl, arylthio or aryl-lower alkylthio group, or an arylsulphonyl group, a triarylmethyl radical, or an organic silyl or stannyl group, it being possible for such a protecting group to be analogous to those of a correspondingly protected amino group in an acyl radical of the formula IA.

A bivalent amino-protecting group formed by the radicals $R_1^a$ and $R_1^b$ together is especially the bivalent acyl radical of an organic dicarboxylic acid, preferably having up to 18 carbon atoms, more especially the diacyl radical of an aliphatic or aromatic dicarboxylic acid, for example the acyl radical of a lower alkanedicarboxylic acid or lower alkenedicarboxylic acid, such as succinyl, or of an o-arylenedicarboxylic acid, such as phthaloyl, or also the acyl radical of an α-aminoacetic acid preferably substituted in the α-position, for example containing an aromatic or heterocyclic radical, the amino group being linked to the nitrogen atom by way of a methylene radical that is preferably substituted, for example that contains two lower alkyl groups, such as methyl groups, for example a 1-oxo-3-aza-1,4-butylene radical, especially substituted in the 2-position, for example containing optionally substituted phenyl or thienyl, and optionally mono- or disubstituted in the 4-position by lower alkyl such as methyl, for example 4,4-dimethyl-2-phenyl-1-oxo-3-aza-1,4-butylene.

The radicals $R_1^a$ and $R_1^b$ together may also represent an organic ylidene radical, such as an aliphatic, cycloaliphatic, cycloaliphatic-aliphatic or araliphatic ylidene radical, preferably having up to 18 carbon atoms.

A protected carboxyl group of the formula —C(=O)—$R_2$ is especially an esterified carboxyl group, in which $R_2$ represents a hydroxy group etherified by an organic radical or an organic silyl or stannyl group. Organic radicals, also as substituents in organic silyl or stannyl groups, are aliphatic, cycloaliphatic, cycloaliphatic-aliphatic, aromatic or araliphatic radicals, especially optionally substituted hydrocarbon radicals of this kind, or alternatively heterocyclic or heterocyclic-aliphatic radicals, preferably having up to 18 carbon atoms.

An etherified hydroxy group $R_2$ forms, together with the carbonyl grouping, a carboxyl group that can preferably readily be split, for example by reduction, such as by hydrogenolysis, or by solvolysis, such as acidolysis, or by hydrolysis, and also by oxidation, or one that can readily be converted into a different functionally modified carboxyl group, such as an esterified carboxyl group that can be converted into a different esterified carboxyl group or into a hydrazinocarbonyl group. An $R_2$ group of this kind is, for example, 2-halo-lower alkoxy, the halogen preferably having an atomic weight of more than 19, for example 2,2,2-trichloroethoxy or 2-iodoethoxy, or 2-chloroethoxy or 2-bromoethoxy which can readily be converted into the latter, or 2-lower alkylsulphonyl-lower alkoxy, for example 2-methylsulphonylethoxy. The group $R_2$ is also a methoxy group polysubstituted by optionally substituted hydrocarbon radicals, especially saturated aliphatic or aromatic hydrocarbon radicals, such as lower alkyl, for example methyl, and/or phenyl, or a methoxy group monosubstituted by an unsaturated aliphatic hydrocarbon radical, such as lower alkenyl, for example 1-lower alkenyl, such as vinyl, by a carbocyclic aryl group having electron-donating substituents or by a heterocyclic group of aromatic character having oxygen or sulphur as ring member; such as tert.-lower alkoxy, for example tert.-butoxy or tert.-pentyloxy, optionally substituted diphenylmethoxy, for example diphenylmethoxy or 4,4'-dimethoxydiphenylmethoxy, lower alkenyloxy, especially 2-lower alkenyloxy, for example allyloxy, lower alkoxyphenyl-lower alkoxy, for example lower alkoxy-benzyloxy, such as methoxybenzyloxy (methoxy being especially in the 3-, 4- and/or 5-position), especially 3- or 4-methoxybenzyloxy, 3,4-dimethoxybenzyloxy, or, above all, nitrobenzyloxy, for example 4-nitrobenzyloxy, 2-nitrobenzyloxy or 4,5-dimethoxy-2-nitrobenzyloxy, or furfuryloxy, such as 2-furfuryloxy. $R_2$ can also be 2-oxa- or 2-thia-cycloalkoxy or 2-oxa- or 2-thia-cycloalkenyloxy having from 5 to 7 ring members, such as 2-tetrahydrofuryloxy, 2-tetrahydropyranyloxy or 2,3-dihydro-2-pyranyloxy or a corresponding thia group, or arylcarbonylmethoxy, aryl representing especially an optionally substituted phenyl group, for example phenacyloxy, or $R_2$ forms, together with the —C(=O)— grouping, an activated ester group and is, for example, nitrophenoxy, for example 4-nitrophenoxy or 2,4-dinitrophenoxy, or polyhalophenoxy, for example pentachlorophenoxy. $R_2$ may alternatively be unbranched lower alkoxy, for example methoxy or ethoxy.

An organic silyloxy or stannyloxy group $R_2$ is especially a silyloxy or stannyloxy group substituted by from 1 to 3 optionally substituted hydrocarbon radicals, preferably having up to 18 carbon atoms. This group contains, as substituents, preferably aliphatic, cycloaliphatic, aromatic or araliphatic hydrocarbon radicals, optionally substituted, for example substituted by lower alkoxy, such as methoxy, or by halogen, such as chlorine; such as lower alkyl, halo-lower alkyl, cycloalkyl, phenyl or phenyl-lower alkyl, and is especially tri-lower alkylsilyloxy, for example trimethylsilyloxy, halo-lower alkoxylower alkylsilyloxy, for example chloromethoxymethylsilyloxy, or tri-lower alkylstannyloxy, for example tri-n-butylstannyloxy.

The group $R_2$ can also be an etherified hydroxy group that forms, together with the carbonyl grouping —C(=O)—, an esterified carboxyl group that can be split under physiological conditions, especially an acyloxymethoxy group, in which acyl denotes, for example, the radical of an organic carboxylic acid, especially an optionally substituted lower alkanecarboxylic acid, or in which acyloxymethyl forms the radical of a lactone. Hydroxy groups etherified in this manner are lower alkanoyloxymethoxy, for example acetoxymethoxy or pivaloyloxymethoxy, amino-lower alkanoyloxymethoxy, especially α-amino-lower alkanoyloxymethoxy, for example glycyloxymethoxy, L-valyloxymethoxy, L-leucyloxymethoxy, or also phthalidyloxy.

A radical $R_2$ forming together with a —C(=O)— grouping an optionally substituted hydrazinocarbonyl group is, for example, hydrazino or 2-lower alkylhydrazino, for example 2-methylhydrazino.

Salts are especially those of compounds of the formula I or II with an acidic grouping, such as a carboxy group, especially metal or ammonium salts, such as alkali metal and alkaline earth metal salts, for example sodium, potassium, magnesium or calcium salts, and also ammonium salts with ammonia or suitable organic amines, the most suitable for the salt formation being aliphatic, cycloaliphatic, cycloaliphatic-aliphatic and araliphatic primary, secondary or tertiary, mono-, di- or poly-amines, as well as heterocyclic bases, such as lower alkylamines, for example triethylamine, hydroxy-lower alkylamines, for example 2-hydroxyethylamine, di-(2-hydroxyethyl)amine or tri-(2-hydroxyethyl)amine, basic aliphatic esters of carboxylic acids, for example 4-aminobenzoic acid 2-diethylaminoethyl ester, lower alkyleneamines, for example 1-ethylpiperidine, cycloalkylamines, for example bicyclohexylamine, or benzylamines, for example N,N'-dibenzylethylenediamine, and also bases of the pyridine type, for example pyridine, collidine or quinoline. Compounds of the formula I or II that contain a basic group can also form acid addition salts, for example with inorganic acids, such as hydrochloric acid, sulphuric acid or phosphoric acid, or with suitable organic carboxylic or sulphonic acids, for example trifluoroacetic acid or p-toluenesulphonic acid. Compounds of the formula I or II having an acidic group and a basic group may also exist in the form of internal salts, that is to say, in zwitterionic form. 1-Oxides or compounds of the formula I or II with saltforming groups can likewise form salts, as described above. In a starting material of the formula II, the preferred salts are those which do not disturb the reduction reaction.

The invention relates especially to the production of compounds of the formula I, in which $R_1^a$ represents hydrogen or preferably an acyl radical present in an N-acyl derivative of a 6β-amino-penam-3-carboxylic acid compound or a 7β-amino-3-cephem-4-carboxylic acid compound, which derivative can be produced by fermentation (that is to say, one which is naturally occurring) or bio-synthetically, semi-synthetically or entirely synthetically, such as one of the above-mentioned acyl radicals of the formula (IA), wherein, in this formula, $R_a$, $R_b$ and $R_c$ have especially the meanings emphasised above and $R_1^b$ represents hydrogen, or in which $R_1^a$ and $R_1^b$ together represent a 1-oxo-3-aza-1,4-butylene radical substituted in the 2-position preferably, for example, by an aromatic or heterocyclic radical, such as a phenyl radical, and in the 4-position preferably, for example, by two lower alkyl radicals, such as methyl radicals, $R_2$ represents a hydroxy group etherified by an organic radical or an organic silyl or stannyl group, or an optionally substituted hydrazino group, and 1-oxides thereof, as well as salts of such compounds with salt-forming groups, from correspondingly substituted compounds of the formula II, 1-oxides or salts thereof.

In a compound of the formula I or II, in a 1-oxide or in a salt of such a compound with salt-forming groups, $R_1^a$ represents especially hydrogen or an acyl radical of the formula IA
in which (1)
  $R_a$ has especially the meanings emphasised above and represents, for example, phenyl, thienyl, furyl, cyclohexadienyl or cyclohexenyl all optionally substituted by hydroxy, protected hydroxy, lower alkoxy, lower alkanoyloxy, carbamoyloxy, halogen, lower alkylsulphonylamino or aminomethyl, or thiazolyl substituted by amino, lower alkylamino or protected amino,
  $R_b$ represents hydrogen, and
  $R_c$ represents hydrogen, optionally protected hydroxy, optionally protected amino or optionally protected carboxyl or sulpho,
or in which (2)
  $R_a$ represents optionally protected 3-amino-3-carboxypropyl, cyano, 1-tetrazolyl, phenoxy optionally substituted in the same manner as phenyl, or 4-pyridylthio, and
  $R_b$ and $R_c$ represent hydrogen,
or in which (3)
  $R_a$ represents phenyl, thienyl or furyl, or thiazolyl substituted by amino, lower alkylamino or protected amino, and
  $R_b$ and $R_c$ together represent syn-lower alkoxyimino,
  $R_1^b$ represents hydrogen, and
  $R_2$ represents optionally α-poly-branched lower alkoxy, for example methoxy or tert.-butoxy, or 2-halo-lower alkoxy, for example 2,2,2-trichloroethoxy, 2-iodoethoxy, or 2-chloroethoxy or 2-bromoethoxy which can readily be converted into the latter, or alternatively phenacyloxy, 1-phenyl-lower alkoxy having from 1 to 3 phenyl radicals optionally substituted by lower alkoxy and/or by nitro, for example 4-methoxybenzyloxy, 4-nitrobenzyloxy, 2-nitro-4,5-dimethoxybenzyloxy, diphenylmethoxy, 4,4'-dimethoxydiphenylmethoxy or trityloxy, lower alkanoyloxymethoxy, for example acetoxymethoxy or pivaloyloxymethoxy, α-amino-lower alkanoyloxymethoxy, for example glycyloxymethoxy, 2-phthalidyloxy, or alternatively lower alkenyloxy, especially 2-lower alkenyloxy, for example allyloxy.

The invention relates especially to the production of compounds of the formula I, in which $R_1^a$ represents hydrogen or especially an acyl group of the formula IA, in which (1)
  $R_a$ represents phenyl, hydroxyphenyl, for example 3- or 4-hydroxyphenyl, lower alkylsulphonylaminophenyl, for example 3-methylsulphonylaminophenyl, aminomethylphenyl, for example 2-aminomethylphenyl, thienyl, for example 2- or 3-thienyl, aminomethylthienyl, for example 5-aminomethyl-2-thienyl, furyl, for example 2-furyl, aminomethylfuryl, for example 5-aminomethyl-2-furyl, 1,4-cyclohexadienyl, aminomethyl-1,4-cyclohexadienyl, for example 2-aminomethyl-1,4-cyclohexadienyl, 1-cyclohexenyl, aminomethyl-1-cyclohexenyl, for example 2-aminomethyl-1-cyclohexenyl, 2-amino-4-thiazolyl or 2-lower alkylamino-4-thiazolyl, wherein, in the above radicals, hydroxy and/or amino can be protected, for example, by acyl, such as optionally halogenated lower alkoxycarbonyl, for example tert.-butoxycarbonyl, or 2,2,2-trichloroethoxycarbonyl, $R_b$ represents hydrogen, and $R_c$ represents hydrogen, amino, or alternatively protected amino, such as acylamino, for example β-poly-branched lower alkoxycarbonylamino, such as tert.-butoxycarbonylamino or 2-halo-lower alkoxycarbonylamino, for example 2,2,2-trichloroethoxycarbonylamino, 2-iodoethoxycarbonylamino or 2-bromoethoxycarbonylamino, or optionally lower alkoxysubstituted and/or nitro-substituted phenyllower alkoxycarbonylamino, for example 4-methoxybenzyloxycarbonylamino or diphenylmethoxycarbonylamino, or represents hydroxy, or alternatively protected hydroxy, such as acyloxy, for example β-poly-branched lower alkoxycarbonyloxy, such as tert.-butoxycarbonyloxy, or 2-halo-lower alkoxycarbonyloxy, such as 2,2,2-trichloroethoxycarbonyloxy, 2-iodoethoxycarbonyloxy or 2-bromoethoxycarbonyloxy, or represents carboxyl or sulpho optionally esterified, for example by lower alkyl, or in which (2)

$R_a$ represents 3-amino-3-carboxypropyl, in which amino can be protected, for example in the same manner as the above amino group $R_c$, and carboxy can be protected, for example in the same manner as the 4-carboxy group —C(=O)—$R_2$, cyano, 1-tetrazolyl, phenoxy or 4-pyridylthio, and $R_b$ and $R_c$ represent hydrogen, or in which (3)

$R_a$ represents phenyl, 2-thienyl, 2-furyl, 2-amino-4-thiazolyl, 2-lower alkylamino-4-thiazolyl, for example 2-ethylamino-4-thiazolyl, wherein amino can be protected, for example by acyl, such as optionally halogenated lower alkoxycarbonyl, for example tert.-butoxycarbonyl or 2,2,2-trichloroethoxycarbonyl, and $R_b$ and $R_c$ together represent syn-lower alkoxyimino, such as syn-methoxyimino, $R_1{}^b$ represents hydrogen, and $R_2$ represents especially methoxy, α-poly-branched lower alkoxy, for example tert.-butoxy, 2-halo-lower alkoxy, for example 2,2,2-trichloroethoxy, 2-iodoethoxy or 2-bromoethoxy, or diphenylmethoxy optionally substituted, for example, by lower alkoxy, such as methoxy, for example diphenylmethoxy or 4,4'-dimethoxydiphenylmethoxy, or 4-nitrobenzyloxy, or alternatively tri-lower alkylsilyloxy, for example trimethylsilyloxy, as well as 2-lower alkenyloxy, for example allyloxy, as well as 1-oxides and salts thereof from correspondingly substituted compounds of the formula II, 1-oxides or salts thereof.

The invention relates especially to the production of 7β-acetylamino-3-hydroxycepham-4-carboxylic acid compounds, in which acetyl is substituted by the radicals $R_a$, $R_b$ and $R_c$, in which (1)

$R_a$ represents phenyl, 2- or 3-thienyl, 2- or 3-furyl, $R_b$ represents hydrogen or amino optionally protected, for example, as described above, and $R_c$ represents hydrogen, or in which (2)

$R_a$ represents phenoxy, and $R_b$ and $R_c$ each represents hydrogen, or in which (3)

$R_a$ represents phenyl or 2-amino-4-thiazolyl, 2-lower alkylamino-4-thiazolyl, for example 2-ethylamino-4-thiazolyl, wherein amino can be protected, for example, by acyl, such as optionally halogenated lower alkoxycarbonyl, for example tert.-butoxycarbonyl or 2,2,2-trichloroethoxycarbonyl, and $R_b$ and $R_c$ together represent syn-lower alkoxyimino, for example syn-methoxyimino, and $R_2$ represents an esterified hydroxy group, especially lower alkoxy, for example methoxy or tert.-butoxy, 2-halo-lower alkoxy, for example 2,2,2-trichloroethoxy, nitrobenzyloxy, for example 4-nitrobenzyloxy, or diphenylmethoxy, 1-oxides and salts of such compounds with salt-forming groups from correspondingly substituted compounds of the formula II, 1-oxides or salts thereof.

Suitable complex borohydrides for the process according to the invention are, for example, alkali metal borohydrides, for example lithium or sodium borohydride, or also other metal borohydrides, for example zinc borohydride, or borohydrides in which from one to three hydrogen atoms are replaced by cyano or by acyloxy groups, for example by optionally halogenated alkanoyloxy groups, for example formyloxy, acetoxy, propionyloxy, palmityloxy, monochloroacetoxy or trifluoroacetoxy, or by aromatic acyloxy groups, for example benzoyloxy, or the like, or also by lower alkoxy, for example methoxy or ethoxy, for example sodium cyanoborohydride ($NaBH_3CN$), sodium triacetoxyborohydride [$NaBH(CH_3COO)_3$] or sodium trimethoxyborohydride [$NaBH(OCH_3)_3$]. The borohydride is used in an at least equivalent amount, preferably in an amount of from 1 to 10 equivalents, optionally in portions, calculated on the starting material of the formula II.

The organic acids that may be used according to the invention are organic carboxylic acids. Suitable acids are especially aliphatic, cycloaliphatic or aromatic carboxylic acids having up to 18 carbon atoms, which may optionally be substituted, for example by halogen, such as chlorine, lower alkoxy, such as methoxy, aryl, such as phenyl, or by nitro. Aliphatic carboxylic acids are, for example, optionally substituted lower alkanecarboxylic acids, for example formic, acetic, propionic, butyric, chloroacetic, trifluoroacetic or phenylacetic acid, or higher alkanecarboxylic acids, for example palmitic acid. Cycloaliphatic carboxylic acids are, for example, optionally substituted cyclopentanecarboxylic acid or cyclohexanecarboxylic acid. Aromatic carboxylic acids are, for example, benzoic acid or benzoic acid substituted as stated above, for example chlorobenzoic acid, methoxybenzoic acid or nitrobenzoic acid.

Preferred organic acids are those which are liquid at the reaction temperature, especially the optionally halogenated lower alkanecarboxylic acids, such as formic acid, trifluoroacetic acid and especially acetic acid. The acids mentioned are used in amounts of at least one mole per mole of compound of the formula II used, preferably in a large excess, optionally as solvents.

The reduction according to the invention is carried out either in one of the above-mentioned organic liquid acids alone or with the addition of a further solvent. Suitable additional solvents are inert solvents which do not disturb the reduction, especially polar solvents, such as halogenated hydrocarbons, for example methylene chloride, ethers, for example diethyl ether, lower alkylene glycol di-lower alkyl ethers, for example dimethoxyethane or diethylene glycol dimethyl ether, cyclic ethers, for example dioxan or tetrahydrofuran, carboxylic acid amides, for example dimethylformamide, di-lower alkyl sulphoxides, for example dimethyl sulphoxide, or lower alkanols, for example methanol, ethanol or tert.-butanol, or mixtures thereof. If necessary, the reaction is carried out in an inert gas atmosphere, for example an argon or nitrogen atmosphere.

The reaction temperature is between −20° and 80° and preferably between 0° and 30°.

A preferred variation is reduction with sodium borohydride in the presence of formic acid or glacial acetic acid at approximately 15° to 20°.

In compounds obtainable according to the invention, the functional substituents in the radicals $R_1^A$, $R_1^b$ and/or $R_2$ can be converted into different functional groups.

Compounds of the formula I that are obtained can be converted into their 1-oxides in a manner known per se by oxidation with suitable oxidising agents, such as hydrogen peroxide or peracids, for example peracetic acid or 3-chloroperbenzoic acid. 1-oxides of compounds of the formula I that are obtained can be reduced to the corresponding compounds of the formula I in a manner known per se by reduction with suitable reducing agents, such as phosphorus trichloride. In these reactions, care must be taken that, if necessary, free functional groups are protected and, if desired, subsequently liberated.

Salts of compounds of the formula I can be produced in a manner known per se. For example, salts of such compounds with acidic groups can be formed, for example, by treating with metal compounds, such as alkali metal salts of suitable carboxylic acids, for example the sodium salt of α-ethylcaproic acid, or with ammonia or with a suitable organic amine, stoichiometric amounts or only a slight excess of the salt-forming agent preferably being used. Acid addition salts of compounds of the formula I with basic groupings are obtained in the usual manner, for example by treating with an acid or a suitable anion exchange reagent. Internal salts of compounds of the formula I that contain, for example, a salt-forming amino group and a free carboxyl group can be formed, for example, by neutralising salts, such as acid addition salts, to the isoelectric point, for example with weak bases, or by treating with liquid ion exchangers. Salts of 1-oxides of compounds of the formula I with salt-forming groups can be produced in an analogous manner.

Salts can be converted into the free compounds in the usual manner: metal and ammonium salts can be converted, for example, by treating with suitable acids, and acid addition salts, for example, by treating with a suitable basic agent.

Mixtures of isomers that are obtained can be separated into the individual isomers according to methods known per se. Mixtures of diastereoisomeric isomers, can be separated, for example, by fractional crystallisation, adsorption chromatography (column or thin-layer chromatography) or other suitable separating processes. Racemates obtained can be separated into the antipodes in the usual manner, optionally after introducing suitable salt-forming groupings, for example by forming a mixture of diastereoisomeric salts with optically active salt-forming agents, separating the mixture into the diastereoisomeric salts and converting the salts into the free compounds, or by fractional crystallisation from optically active solvents.

The process also includes those embodiments in which compounds formed as intermediates are used as starting materials and the remaining process steps are carried out using these, or the process is interrupted at any stage; furthermore, starting materials may be used in the form of derivatives or formed during the reaction.

The starting materials used and the reaction conditions are preferably so chosen that the compounds mentioned at the beginning as being especially preferred are obtained.

The starting compounds of the formula II and 1-oxides and salts thereof are known or can be produced in a manner known per se, for example in a manner analogous to that described in German Offenlegungsschrift Nos. 2,331,148, 2,506,330 or 2,606,196.

The end products of the formula I and 1-oxides and salts thereof can be converted into antibiotically active 7β-acylamido-3-cephem-4-carboxylic acids, for example in a manner analogous to that described in Austrian Patent Specification No. 327,381.

The following Examples illustrate the invention. Temperatures are given in degrees Centigrade.

EXAMPLE 1

3-hydroxy-7β-phenoxyacetylamino-cepham-4α-carboxylic acid diphenylmethyl ester (a) 1.30 g of sodium borohydride are added in portions to a solution of 35.4 g of 3-hydroxy-7β-phenoxyacetylamino-3-cephem-4-carboxylic acid diphenylmethyl ester (crude product) in a mixture of 270 ml of dimethylformamide and 70 ml of glacial acetic acid in a stream of nitrogen while stirring and cooling with ice at approximately 15° to 20°. The reaction mixture is further stirred for one hour at room temperature, poured onto a mixture of ice and 2 N hydrochloric acid and extracted with ethyl acetate. The organic phase is washed successively with 2 N hydrochloric acid, water, saturated, aqueous sodium bicarbonate solution and saturated, aqueous sodium chloride solution, dried over sodium sulphate and concentrated in vacuo. The residue is substantially freed from dimethylformamide under a high vacuum and recrystallised from ethyl acetate and a little diethyl ether. The title compound is obtained which has a melting point of 167°–170°; Rf~0.47 (silica gel; toluene/ethyl acetate 1:1); $[\alpha]_D^{20} = +88° \pm 1°$ (in chloroform, c=0.526%); IR spectrum (in $CH_2Cl_2$): Absorption bands up to 3580; 3410; 1780; 1740; 1695; 1600; 1518; 1494 $cm^{-1}$.

Alternative reaction conditions:

(b) 940 mg (10 equivalents) of sodium borohydride are added in portions to a solution of 5.16 g of 3-hydroxy-7β-phenoxyacetylamino-3-cephem-4-carboxylic acid diphenylmethyl ester (crude product) in 51 ml of glacial acetic acid in a stream of nitrogen while stirring and cooling with ice at approximately 15°. The reaction mixture is further stirred for one hour at room temperature, poured onto a mixture of ice and 2 N hydrochloric acid and extracted with ethyl acetate. The organic phase is washed with water and saturated, aqueous sodium chloride solution, dried over sodium sulphate and concentrated in vacuo. The residue is recrystallised from methylene chloride and diethyl ether. The title compound having the properties mentioned under (a) is obtained.

(c) In the same manner as that described under (b), 516 mg of 3-hydroxy-7β-phenoxyacetylamino-3-cephem-4-carboxylic acid diphenylmethyl ester (crude product) in 5.1 ml of glacial acetic acid are reduced with 94 mg of sodium borohydride and worked up. The title compound having the properties mentioned under (a) is obtained.

(d) In the same manner as that described under (a), 111 g of 3-hydroxy-7β-phenoxyacetylamino-3-cephem-4-carboxylic acid diphenylmethyl ester (crude product) in a mixture of 640 ml of dimethylformamide and 160 ml of glacial acetic acid are reduced with 4.5 g of sodium borohydride and worked up. The title compound having the properties mentioned under (a) is obtained.

(e) 28.4 mg of sodium borohydride are added to a solution of 516 mg of 3-hydroxy-7β-phenoxyacetylamino-3-cephem-4-carboxylic acid diphenylmethyl ester in 4 ml of dimethylformamide and 1 ml of formic acid at room temperature. After stirring the reaction mixture for one hour at room temperature, it is poured onto a mixture of ice and 2 N hydrochloric acid and extracted with ethyl acetate. The combined organic phases are washed successively with water, three times with saturated sodium bicarbonate solution and saturated, aqueous sodium chloride solution, dried over sodium sulphate and concentrated in vacuo. The residue is substantially freed from dimethylformamide under a high vacuum. The resulting white foam (580 mg) is subjected to chromatography on preparative silica gel thick-layer plates with toluene/ethyl acetate 1:1 and yields 403 mg of the title compound.

(f) A reduction experiment carried out analogously and parallel to (e) without the formic acid yielded only 25 mg of the title compound.

Preparation of the starting material: The starting materials used in Examples 1(a) to 1(e) can be prepared, for example, in the following manner:

(i) 24.8 ml of methanesulphonyl chloride and, subsequently, 43.8 ml of triethylamine are added under nitrogen to a solution of 107.68 g of 2-[4-(p-toluenesulphonylthio)-3-phenoxyacetamido-2-oxoazetidin-1-yl]-3-hydroxycrotonic acid diphenylmethyl ester in 1.6 liters of dry methylene chloride, cooled to −10°. After 20 minutes, 40.8 ml of freshly distilled pyrrolidine are added and the mixture is stirred for a further 2½ hours at −10°. The reaction solution is washed successively with 0.1 N hydrochloric acid, water and saturated, aqueous sodium chloride solution, dried over sodium sulphate and concentrated by evaporation in vacuo. The residue is dried to a foam and yields a mixture consisting of the faintly yellow 2-[4-(p-toluenesulphonylthio)-3-phenoxyacetamido-2-oxoazetidin-1-yl]-3-(1-pyrrolidinyl)-crotonic acid diphenylmethyl ester and the corresponding isocrotonic acid diphenylmethyl ester, which is used in this form in the next step.

(ii) A solution of 139.32 g (160 mmol) of a mixture consisting of the 2-[4-(p-toluenesulphonylthio)-3-phenoxyacetamido-2-oxoazetidin-1-yl]-3-(1-pyrrolidinyl)-crotonic acid diphenylmethyl ester and the corresponding isocrotonic acid ester in 1350 ml of dry acetonitrile is heated at 80° for approximately 6 hours under nitrogen until it is no longer possible to detect any starting material by thin layer-chromatography (silica gel; toluene/ethyl acetate 1:1). The heating bath is removed, the reaction mixture containing the 7β-phenoxyacetamido-3-(1-pyrrolidinyl)-3-cephem-4-carboxylic acid diphenylmethyl ester is left to cool for a further 1½ hours, 550 ml of 0.1 N hydrochloric acid are added and the mixture is further stirred for 8½ hours at room temperature. The reaction mixture is diluted with ethyl acetate, the water is separated off, the organic phase is washed twice with 2 N hydrochloric acid and three times with water, dried over sodium sulphate, concentrated by evaporation in vacuo and dried under a high vacuum. The residue, containing the 7β-phenoxyacetamido-3-hydroxy-3-cephem-4-carboxylic acid diphenylmethyl ester, is used in the next step without further purification.

EXAMPLE 2

The following compounds can be obtained in a manner analogous to the processes described in Examples 1(a) to 1(e) starting from the corresponding 3-hydroxy-3-cephem-4-carboxylic acid esters:

7β-phenoxyacetylamino-3-hydroxycepham-4-carboxylic acid tert.-butyl ester,
7β-phenoxyacetylamino-3-hydroxycepham-4-carboxylic acid trichloroethyl ester,
7β-phenoxyacetylamino-3-hydroxycepham-4-carboxylic acid benzyl ester,
7β-phenoxyacetylamino-3-hydroxycepham-4-carboxylic acid p-methoxybenzyl ester,
7β-phenoxyacetylamino-3-hydroxycepham-4-carboxylic acid p-nitrobenzyl ester,
7β-phenylacetylamino-3-hydroxycepham-4-carboxylic acid diphenylmethyl ester,
7β-phenylacetylamino-3-hydroxycepham-4-carboxylic acid tert.-butyl ester,
7β-phenylacetylamino-3-hydroxycepham-4-carboxylic acid trichloroethyl ester,
7β-phenylacetylamino-3-hydroxycepham-4-carboxylic acid benzyl ester,
7β-phenylacetylamino-3-hydroxycepham-4-carboxylic acid p-methoxybenzyl ester,
7β-phenylacetylamino-3-hydroxycepham-4-carboxylic acid p-nitrobenzyl ester,
7β-thien-2- or -3-ylacetylamino-3-hydroxycepham-4-carboxylic acid diphenylmethyl ester.
7β-thien-2- or -3-ylacetylamino-3-hydroxycepham-4-carboxylic acid tert.-butyl ester,
7β-thien-2- or -3-ylacetylamino-3-hydroxycepham-4-carboxylic acid trichloroethyl ester,
7β-thien-2- or -3-ylacetylamino-3-hydroxycepham-4-carboxylic acid benzyl ester,
7β-thien-2- or -3-ylacetylamino-3-hydroxycepham-4-carboxylic acid p-methoxybenzyl ester,
7β-thien-2- or -3-ylacetylamino-3-hydroxycepham-4-carboxylic acid p-nitrobenzyl ester,
7β-fur-2- or -3-ylacetylamino-3-hydroxycepham-4-carboxylic acid diphenylmethl ester,
7β-fur-2- or -3-ylacetylamino-3-hydroxycepham-4-carboxylic acid tert.-butyl ester, 7β-fur-2- or -3-ylacetylamino-3-hydroxycepham-4-carboxylic acid trichloroethyl ester,
7β-fur-2- or -3-ylacetylamino-3-hydroxycepham-4-carboxylic acid benzyl ester,
7β-fur-2- or -3-ylacetylamino-3-hydroxycepham-4-carboxylic acid p-methoxybenzyl ester,
7β-fur-2- or -3-ylacetylamino-3-hydroxycepham-4-carboxylic acid p-nitrobenzyl ester,
7β-(5-diphenylmethoxycarbonyl-5-tert.-butoxycarbonylamino-valerylamino)-3-hydroxycepham-4-carboxylic acid diphenylmethyl ester, 7β-(5-diphenylmethoxycarbonyl-5-tert.-butoxycar-bonylamino-valerylamino)-3-hydroxycepham-4-carboxylic acid tert.-butyl ester,
7β-(5-diphehylmethoxycarbonyl-5-tert.-butoxycar-bonylamino-valerylamino)-3-hydroxycepham-4-carboxylic acid trichloroethyl ester,
7β-(5-diphenylmethoxycarbonyl-5-tert.-butoxycar-bonylamino-valerylamino)-3-hydroxycepham-4-carboxylic acid benzyl ester,
7β-(5-diphenylmethoxycarbonyl-5-tert.-butoxycar-bonylamino-valerylamino)-3-hydroxycepham-4-carboxylic acid p-methoxybenzyl ester,
7β-(5-diphenylmethoxycarbonyl-5-tert.-butoxycar-bonylamino-valerylamino)-3-hydroxycepham-4-carboxylic acid p-nitrobenzyl ester,
7β-(D-N-tert.-butoxycarbonyl-phenylglycylamino)-3-hydroxycepham-4-carboxylic acid diphenylmethyl ester,
7β-(D-N-tert.-butoxycarbonyl-phenylglycylamino)-3-hydroxycepham-4-carboxylic acid tert.-butyl ester,
7β-(D-N-tert.-butoxycarbonyl-phenylglycylamino)-3-hydroxycepham-4-carboxylic acid trichloroethyl ester,
7β-(D-N-tert.-butoxycarbonyl-phenylglycylamino)-3-hydroxycepham-4-carboxylic acid benzyl ester,
7β-(D-N-tert.-butoxycarbonyl-phenylglycylamino)-3-hydroxycepham-4-carboxylic acid p-methoxybenzyl ester,
7β-(D-N-tert.-butoxycarbonyl-phenylglycylamino)-3-hydroxycepham-4-carboxylic acid p-nitrobenzyl ester,
7β-[D-α-tert.-butoxycarbonylamino-α-(1,4-cyclohexadienyl)glycylamino]-3-hydroxycepham-4-carboxylic acid diphenylmethyl ester,
7β[D-α-tert.-butoxycarbonylamino-α-(1,4-cyclohexadienyl)glycylamino]-3-hydroxycepham-4-carboxylic acid tert.-butyl ester,
7β-[D-α-tert.-butoxycarbonylamino-α-(1,4-cyclohexadienyl)glycylamino]-3-hydroxycepham-4-carboxylic acid trichloroethyl ester,
7β-[D-α-tert.-butoxycarbonylamino-α-(1,4-cyclohexadienyl)glycylamino]-3-hydroxycepham-4-carboxylic acid benzyl ester,
7β[D-α-tert.-butoxycarbonylamino-α-(1,4-cyclohexadienyl)glycylamino]-3-hydroxycepham-4-carboxylic acid p-methoxybenzyl ester,
7β-[D-α-tert.-butoxycarbonylamino-α-(1,4-cyclohexadienyl)glycylamino]-3-hydroxycepham-4-carboxylic acid p-nitrobenzyl ester,
7β[2-(2-tert.-butoxycarbonylamino-4-thiazolyl)-2-methoxyiminoacetylamino]-3-hydroxycepham-4-carboxylic acid diphenylmethyl ester,
7β[2-(2-tert.-butoxycarbonylamino-4-thiazolyl)-2-methoxyiminoacetylamino]-3-hydroxycepham-4-carboxylic acid tert.-butyl ester,
7β-[2-(2-tert.-butoxycarbonylamino-4-thiazolyl)-2-methoxyiminoacetylamino]-3-hydroxycepham-4-carboxylic acid trichloroethyl ester,
7β-[2-(2-tert.-butoxycarbonylamino-4-thiazolyl)-2-methoxyiminoacetylamino]-3-hydroxycepham-4-carboxylic acid benzyl ester,
7β[2-(2-tert.-butoxycarbonylamino-4-thiazolyl)2-methoxyiminoacetylamino]-3-hydroxycepham-4-carboxylic acid p-methoxybenzyl ester,
7β-[2-(2-tert.-butoxycarbonylamino-4-thiazolyl)-2-methoxyiminoacetylamino]-3-hydroxycephem-4-carboxylic acid p-nitrobenzyl ester,
7β-amino-3-hydroxycepham-4-carboxylic acid diphenylmethyl ester,
7β-amino-3-hydroxycepham-4-carboxylic acid tert.-butyl ester,
7β-amino-3-hydroxycepham-4-carboxylic acid trichloroethyl ester,
7β-amino-3-hydroxycepham-4-carboxylic acid benzyl ester,
7β-amino-3-hydroxycepham-4-carboxylic acid p-methoxybenzyl ester,
7β-amino-3-hydroxycepham-4-carboxylic acid p-nitrobenzyl ester, as well as 1-oxides thereof, starting from the corresponding 1-oxides.

What is claimed is:

1. Process for the production of 7β-substituted 3-hydroxy-cepham-4-carboxyic acid compounds of the formula

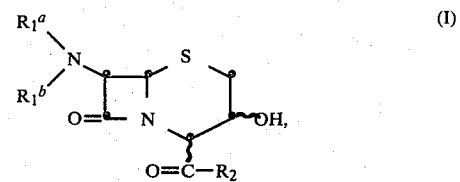

in which
$R_1{}^a$ represents hydrogen or an amino-protecting group $R_1{}^A$, and
$R_1{}^b$ represents hydrogen or an acyl radical Ac having up to 18 carbon atoms or in which
$R_1{}^a$ and $R_1{}^b$ together from a bivalent acyl radical of an organic dicarboxylic acid having up to 18 carbon atoms, and
$R_2$ represents a radical that, together with the carbonyl grouping —C(=O)—, forms a protected carboxyl group, and 1-oxides thereof as well as salts of such compounds with salt-forming groups, from a 7β-substituted 3-hydroxy-3-cephem-4-carboxylic acid compound of the formula

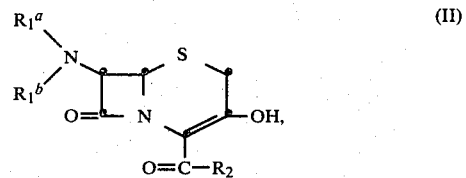

from a 1-oxide or a salt thereof, and a complex borohydride selected from the group consisting of an alkali metal borohydride, zinc borohydride, or such borohydride wherein from one to three hydrogen atoms are replaced by cyano, alkanoyloxy, halogenated alkanoyloxy, benzoyloxy, or lower alkoxy, characterized in that the reduction is carried out in the presence of an organic acid selected from the group consisting of an aliphatic, cycloaliphatic or aromatic carboxylic acid having up to 18 carbon atoms, which may be substituted by halogen, lower alkoxy, phenyl, or nitro.

2. Process for the production of compounds of the formula I, in which $R_1{}^a$ represents hydrogen or an acyl radical having up to 18 carbon atoms and $R_1{}^b$ represents hydrogen, according to claim 1.

3. Process for the production of compounds of the formula I, in which $R_2$ represents a radical that, together with the carbonyl grouping —C(=O)—, forms an esterified carboxyl group selected from the group consisting of 2-halo-lower alkoxy, 2-lower alkylsulphonyl-lower alkoxy, tert.-lower alkoxy, diphenylmethoxy, 4,4'-dimethoxydiphenylmethoxy, lower alkenyloxy, lower alkoxyphenyl-lower alkoxy, nitrobenzyloxy, furfuryloxy, 2-tetrahydrofuryloxy, 2-tetrahydropyranyloxy, 2,3-dihydro-2-pyranyloxy, phenyl-carbonylmethoxy, nitrophenoxy, polyhalogenophenoxy, lower alkoxy, tri-lower-alkylsilyloxy, halo-lower alkoxy-lower alkylsilyloxy, tri-lower alkylstannyloxy, lower alkanoyloxymethoxy, amino-lower alkanoyloxymethoxy, or phthalidyloxy, according to claim 1.

4. Process for the production of compounds of the formula I, in which $R_1{}^a$ represents hydrogen or an acyl group of the formula

in which (1)

$R_a$ represents phenyl, hydroxyphenyl, lower alkylsulphonylaminophenyl, aminomethylphenyl, thienyl, aminomethylthienyl, furyl, aminomethylfuryl, 1,4-cyclohexadienyl, aminomethyl-1,4-cyclohexadienyl, 1-cyclohexenyl, aminomethyl-1-cyclohexenyl, 2-amino-4-thiazolyl or 2-lower alkylamino-4-thiazolyl, wherein, in the above radicals, hydroxy and/or amino can be protected, $R_b$ represents hydrogen, and $R_c$ represents hydrogen, amino, protected amino, hydroxy, protected hydroxy, carboxyl or sulpho optionally esterified, in which (2)

$R_a$ represents 3-amino-3-carboxypropyl, in which amino and carboxy can be protected, cyano, 1-tetrazolyl, phenoxy or 4-pyridylthio, and $R_b$ and $R_c$ represent hydrogen, or in which (3)

$R_a$ represents phenyl, thienyl, furyl, 2-amino-4-thiazolyl, 2-lower alkylamino-4-thiazolyl, wherein amino can be protected, and $R_b$ and $R_c$ together represent syn-lower alkoxyamino, $R_1{}^b$ represents hydrogen, and $R_2$ represents methoxy, α-poly-branched lower alkoxy, 2-halo-lower alkoxy, diphenylmethoxy optionally substituted, by lower alkoxy, 4-nitrobenzyloxy, tri-lower alkylsilyloxy, or 2-lower alkenyloxy, according to claim 1.

5. Process according to claim 1, characterised in that there is used as complex borohydride an alkali metal borohydride.

6. Process according to claim 1, characterised in that there is used as complex borohydride sodium borohydride.

7. Process according to claim 1, characterised in that there is used as organic acid an aliphatic, cycloaliphatic or aromatic carboxylic acid having up to 1 carbon atoms, which may optionally be substituted by halogen, lower alkoxy, phenyl, or by nitro.

8. Process according to claim 1, characterised in that there is used as organic acid an optionally halogenated lower alkanecarboxylic acid.

9. Process according to claim 1, characterised in that sodium borohydride is used in the presence of glacial acetic acid.

10. Process according to claim 1, characterised in that sodium borohydride is used in the presence of formic acid.

11. Process according to claim 1, characterised in that the reduction is carried ou at approximately 15° to 20° C.

12. Process according to claim 1 for the production of 3-hydroxy-7β-phenoxyacetylamino-cepham-4α-carboxylic acid diphenylmethylester from 3-hydroxy-7β-phenoxyacetylamino-3-cephem-4-carboxylic acid diphenylmethylester and sodium borohydride, characterised in that the reduction is carried out in the presence of glacial acetic acid.

13. Process according to claim 1 for the production of 3-hydroxy-7β-phenoxyacetylamino-cepham-4α-carboxylic acid diphenylmethylester from 3-hydroxy-7β-phenoxyacetylamino-3-cephem-4-carboxylic acid diphenylmethylester and sodium borohydride, characterised in that the reduction is carried out in the presence of formic acid.

* * * * *